United States Patent
During

(10) Patent No.: US 10,493,069 B2
(45) Date of Patent: *Dec. 3, 2019

(54) METHODS OF TREATING BEHAVIORAL SYNDROMES USING PIPRADROL

(71) Applicant: Ovid Therapeutics Inc., New York, NY (US)

(72) Inventor: Matthew During, Weston, CT (US)

(73) Assignee: OVID THERAPEUTICS INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,933

(22) Filed: Nov. 8, 2018

(65) Prior Publication Data

US 2019/0076415 A1   Mar. 14, 2019

Related U.S. Application Data

(63) Continuation of application No. 15/788,168, filed on Oct. 19, 2017, now abandoned, which is a continuation of application No. 15/604,776, filed on May 25, 2017, now Pat. No. 9,827,233.

(60) Provisional application No. 62/341,855, filed on May 26, 2016.

(51) Int. Cl.
*A61K 31/4458* (2006.01)
*A61K 45/06* (2006.01)

(52) U.S. Cl.
CPC .......... *A61K 31/4458* (2013.01); *A61K 45/06* (2013.01)

(58) Field of Classification Search
CPC .................................................. A61K 31/4458
See application file for complete search history.

(56) References Cited

U.S. PATENT DOCUMENTS

| | | | |
|---|---|---|---|
| 2,830,083 | A | 4/1958 | Gilbert et al. |
| 3,947,579 | A | 3/1976 | Fuxe |
| 4,084,000 | A | 4/1978 | Fuxe |
| 4,129,652 | A | 12/1978 | Fuxe |
| 8,461,389 | B2 | 6/2013 | Regan et al. |
| 9,351,968 | B1 | 5/2016 | During |
| 9,827,233 | B1 * | 11/2017 | During ................... A61K 45/06 |
| 2010/0016425 | A1 | 1/2010 | Vath |
| 2011/0034562 | A1 | 2/2011 | Regan |
| 2011/0172188 | A1 | 7/2011 | Mouthon et al. |
| 2017/0065572 | A1 | 3/2017 | During |
| 2018/0036298 | A1 | 2/2018 | During |

FOREIGN PATENT DOCUMENTS

| WO | 2008095253 A1 | 8/2008 | |
|---|---|---|---|
| WO | WO-2008095253 A1 * | 8/2008 | ............ A61K 31/19 |
| WO | 2011147889 A1 | 12/2011 | |

OTHER PUBLICATIONS

Kistner et al., "User of Pipradrol in Obstetrics and Gynecology," The New England Journal of Medicine, vol. 254, No. 11, Mar. 15, 1956; pp. 507-510.
Chen et al., J. Pharmacology Experimental Therapeutics (1958), vol. 123, pp. 212-215.
GuideChem, CAS Database, pp. 1-2, Aug. 28, 2009.
Howard D. Fabing, "Clinical Experience with Meratran (A New Central Nervous System Stimmulant)", Diseases of the Nervous System, vol. XVI, No. 1, Jan. 1955; pp. 10-15.
Rickels et al., "Pipradrol in Mild Depression: A Controlled Study", the Journal of Clinical Pharmacology, Feb.-Mar. 1974, pp. 127-133.
White, et al, "Pipradrol and Pipradrol Derivatives", Novel Psychoactive Substances, Elsevier, 2013, Chapter 10; pp. 233-259.
Kistner et al., "Use of Pipradrol in Obstetrics and Gynecology", The New England Journal of Medicine, vol. 254, No. 11, Mar. 15, 1956; pp. 507-510.
Leon Oettinger, Jr., M.D. "Meratran—Preliminary Report of a New Drug for the Treatment of Behavior Disorders in children", Diseases of the Nervous System, Oct. 1955; pp. 299-302.
International Search Report and Written Opinion, dated Oct. 4, 2016, corresponding to International Application No. PCT/US16/50702; 9 total pages.
International Search Report and Written Opinion of the International Searching Authority, dated Jul. 18, 2017, coresponding to International Application No. PCT/US17/34443; 5 total pages.

* cited by examiner

*Primary Examiner* — Svetlana M Ivanova
(74) *Attorney, Agent, or Firm* — Carter, DeLuca & Farrell, LLP

(57) ABSTRACT

Methods of treating behavioral syndromes by administering a pharmaceutical composition of pipradrol or a pharmaceutically acceptable salt thereof are provided. The methods may be used to treat Attention-Deficit Disorder (ADD) and Attention-Deficit Hyperactivity Disorder (ADHD).

16 Claims, No Drawings

METHODS OF TREATING BEHAVIORAL SYNDROMES USING PIPRADROL

CROSS-REFERENCE TO RELATED APPLICATION

This application is a continuation of U.S. patent application Ser. No. 15/788,168, filed Oct. 19, 2017, which is a continuation of U.S. patent application Ser. No. 15/604,776, filed May 25, 2017, now U.S. Pat. No. 9,827,233, issued Nov. 28, 2017, which claims the benefit of and priority to U.S. Provisional Application Ser. No. 62/341,855, filed on May 26, 2016, the entire contents of which are herein incorporated by reference.

TECHNICAL FIELD

Methods of using a composition including pipradrol, a derivative thereof, or a pharmaceutically acceptable salt thereof for the treatment of behavioral syndromes in a subject in need thereof.

BACKGROUND

Pipradrol is a mild central nervous system stimulant that acts on both dopamine and norepinephrine reuptake. It was originally marketed as Meratran® (Wm. S. Merrell Co of Cincinnati Ohio) and also in combination with several vitamins as Alertonic® Elixir. Pipradrol was considered an "energetic" when it first came to market in the mid to late 1950's and used for obesity, narcolepsy, and depression. Pipradrol has also been used in the setting of obstetric and gynecological practice, with multiple benefits, for example improving nausea and vomiting, premenstrual symptoms, post-partum psychosis, and menopausal-associated depression Kistner and Duncan, *The New England Journal of Medicine* 254, 507-510 (1956).

There is limited evidence that suggests pipradrol may have some efficacy in behavioral disorders in children. Oettinger, *Diseases of the Nervous System* 16, 299-302 (1955). The report concludes that the action of pipradrol lies in increasing the attention span and decreasing irritability with a resultant increase in function. However, pipradrol has been associated with side effects such as anxiety and alertness at bedtime. Fabing, *Diseases of the Nervous System* 10-15 (January 1955). In addition, although some anticonvulsant activity has been suggested, high doses of pipradrol may cause incoordinated activity and ataxia, followed by tremors and clonic convulsions. Following the Kefauver-Harris amendments to the FDA act in 1962, pipradrol was one of thousands of drugs that were assessed by special committees to define whether there was sufficient safety and efficacy to remain an approved drug. This process was called the Drug Efficacy Study Initiative or DESI. The committee which reviewed pipradrol included the psychiatrist Karl Rickels, who had published a study on 111 individuals with depression, in which pipradrol was not superior to placebo (Rickels et al., *The Journal of Clinical Pharmacology* 14, 127-133; 1974). As a result, pipradrol was removed from the FDA register of approved drugs.

There remains a need for improved methods of treating behavioral syndromes.

SUMMARY

Methods of treating behavioral syndromes by administering to a patient in need thereof a pharmaceutical composition of pipradrol or a pharmaceutically acceptable salt thereof.

The methods and compositions may be used for treating behavioral syndromes including Attention Deficit Disorder (ADD), Attention-Deficit Hyperactivity Disorder (ADHD), Hyperkinetic Child Syndrome, Minimal Brain Damage, Minimal Cerebral Dysfunction, Minor Cerebral Dysfunction, and narcolepsy.

Generally, the pipradrol or derivative thereof is administered to a patient diagnosed with a behavioral syndrome in a daily dosage range of about 0.1 mg to about 50 mg. In embodiments, an infant may be administered pipradrol or pharmaceutically acceptable salt thereof in a daily dosage range of about 0.2 mg to about 1 mg. In embodiments, a non-infant child may be administered pipradrol or pharmaceutically acceptable salt thereof in a daily dosage range of about 1 mg to about 5 mg. In embodiments, an adult may be administered pipradrol or pharmaceutically acceptable salt thereof in a daily dosage range of about 5 mg to about 10 mg.

DETAILED DESCRIPTION

Provided herein are methods and compositions for treating behavioral syndromes by administering to a patient in need thereof a pharmaceutical composition including pipradrol, a derivative thereof, or a pharmaceutically acceptable salt thereof. In embodiments, the methods and compositions described herein include pipradrol or a pharmaceutically acceptable salt thereof. In embodiments, methods are provided for treatment of Attention Deficit Disorder (previously known as Minimal Brain Dysfunction in Children).

In embodiments, the methods and compositions may be used to treat Attention-Deficit Hyperactivity Disorder (ADHD). The methods and compositions may be used to increase attention, decrease impulsiveness and decrease hyperactivity in patients with ADHD.

In embodiments, methods are provided for treatment of behavioral syndromes such as Hyperkinetic Child Syndrome, Minimal Brain Damage, Minimal Cerebral Dysfunction, Minor Cerebral Dysfunction. The methods and compositions may be used to treat developmentally inappropriate symptoms including moderate-to-severe distractibility, short attention span, hyperactivity, emotional lability, and impulsivity.

In embodiments, the methods and compositions may be used for treating behavioral syndromes including Attention Deficit Disorder, Attention-Deficit Hyperactivity Disorder (ADHD), Hyperkinetic Child Syndrome, Minimal Brain Damage, Minimal Cerebral Dysfunction, Minor Cerebral Dysfunction, and narcolepsy.

In embodiments, the methods and compositions may be used for treating attention function and impulsiveness in ADHD. In embodiments, the methods and compositions may be used for improving attention function in ADHD.

In embodiments, the methods and compositions may be used for treating oppositional defiant disorder, conduct disorder, antisocial personality disorder, borderline personality disorder, primary disorder of vigilance, a mood disorder, bipolar disorder, anxiety disorder, obsessive compulsive disorder, Tourette syndrome, a learning disorder and substance abuse.

The behavioral syndromes included in the methods may be characterized by numerous features including chronic history of short attention span, distractibility, emotional lability, impulsivity, and moderate-to-severe hyperactivity. Nonlocalizing (soft) neurological signs, learning disability, and abnormal EEG may or may not be present, and a diagnosis of central nervous system dysfunction may or may not be warranted. Thus, the methods and compositions may be used to increase the ability to pay attention, stay focused on an activity, and control behavior problems. The methods may also help the patient organize tasks and improve listening skills.

The methods described herein may be useful for treating children and infants, and for treating disorders that onset during infancy or childhood. In embodiments, the subject of the disclosed method is a newborn, a baby, a toddler, a preschooler, a school-age child, a tween, or a teenager. In embodiments, the subject is 18 years old or younger, 12 years old or younger, 10 years old or younger, 8 years old or younger, 6 years old or younger, 4 years old or younger, 2 years old or younger, 1 year old or younger. In embodiments, the subject is an adult that is over eighteen years old.

In embodiments, methods and compositions are provided for treating behavioral syndromes by administering to a patient in need thereof a pharmaceutical composition comprising pipradrol or a pharmaceutically acceptable salt thereof. In embodiments, compounds structurally related to pipradrol or a derivative or analog thereof are administered. Such compounds, can include, for example, desoxypipradrol, diphenylprolinol, 2-(diphenylmethyl)pyrrolidine, or pharmaceutically acceptable salts thereof.

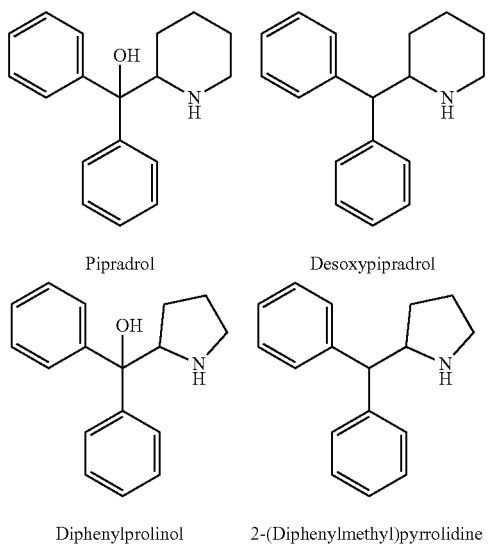

Pipradrol Desoxypipradrol

Diphenylprolinol 2-(Diphenylmethyl)pyrrolidine

Pipradrol, derivatives, analogues and structurally related compounds thereof useful in the disclosed methods includes any form of the compounds, such as the base (zwitter ion), pharmaceutically acceptable salts, e.g., pharmaceutically acceptable acid addition salts, hydrates or solvates of the base or salt, as well as anhydrates, and also amorphous, or crystalline forms.

In embodiments, deuterated pipradrol or deuterated forms of pipradrol derivatives may be used. Deuteration of pharmaceuticals to improve pharmacokinetics (PK), pharmacodynamics (PD), and toxicity profiles, has been demonstrated previously with some classes of drugs. Accordingly the use of deuterium-enriched pipradrol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched pipradrol.

Deuterium enriched pipradrol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments, deuterium enriched pipradrol means that the specified position is enriched with deuterium above the naturally occurring distribution (i.e., above about 0.0156%). In embodiments, deuterium enrichment is, e.g., no less than about 1%, no less than about 5%, no less than about 10%, no less than about 20%, no less than about 50%, no less than about 70%, no less than about 80%, no less than about 90%, or no less than about 98% of deuterium at a specified position. In embodiments, deuterium enrichment may be defined as, e.g., more than about 60%, more than about 65%, more than about 75%, more than about 80%, more than about 85%, more than about 95% deuterium at a specified position.

In embodiments, the pipradrol or a pharmaceutically acceptable salt thereof may include the racemic mixture, as well as compositions including each enantiomer individually. The compositions and methods contemplated herein may provide reduced dosing frequency, reduced adverse events and/or increased efficacy compared to a racemic mixture of pipradrol. In embodiments, compositions and methods that include each enantiomer individually may provide reduced dosing frequency, reduced adverse events and/or increased efficacy compared to the minor enantiomer. Thus, for example, contemplated herein are compositions and methods of treatment that provide the S enantiomer of pipradrol or a pharmaceutically acceptable salt thereof that is substantially free of the R enantiomer. In embodiments, methods and compositions herein include the R enantiomer of pipradrol or a pharmaceutically acceptable salt thereof substantially free of the S enantiomer. By "substantially free" it is meant that the composition includes less than 50% of the minor enantiomer. In embodiments, the compositions and methods herein may include less than about, e.g., 25%, 15%, 10%, 8%, 5%, 3%, 2%, or less than 1% of the minor enantiomer.

In embodiments, the methods and compositions include (S)-pipradrol, or a pharmaceutically acceptable salt thereof. In embodiments, the compositions include more than, e.g., about 75%, about 85%, about 90%, about 95% or about 98% (S)-pipradrol. In embodiments, the compositions include between, e.g., about 50% to about 75%, about 75% to about 100%, about 85% to about 100%, about 90% to about 100%, or about 95% to about 100% (S)-pipradrol.

In embodiments, the methods and compositions herein include (R)-pipradrol, or a pharmaceutically acceptable salt thereof. In embodiments, the compositions include more than, e.g., about 75%, about 85%, about 90%, about 95% or about 98% (R)-pipradrol. In embodiments, the compositions include between, e.g., about 50% to about 75%, about 75% to about 100%, about 85% to about 100%, about 90% to about 100%, or about 95% to about 100% (R)-pipradrol.

In embodiments, pipradrol or a pharmaceutically acceptable salt thereof is administered at dosages ranging from about 0.001 mg/kg and about 10 mg/kg of body weight of a patient in need thereof, e.g., from about 0.01 mg/kg to 2.0 mg/kg at least once a day. For example, dosages may include amounts of pipradrol or a pharmaceutically acceptable salt thereof in the range of about, e.g., 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, and 30 mg being specific examples of doses.

Typically, dosages of pipradrol or pharmaceutically acceptable salts thereof are administered once or twice daily to a patient in need thereof. The methods and compositions described herein may provide reduced dosing frequency and reduced adverse events and/or increased efficacy. In embodiments, the dosage is about, e.g., 0.1-20 mg/day, or 0.2-15 mg/day, or 0.5-10 mg/day, or 0.75-5 mg/day, for example 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, or 10 mg/day. In embodiments, pipradrol, or a derivative or analogue thereof is administered at doses of 0.2 mg to 1 mg in infants or 1-20 mg in adults, once daily.

Methods of treating behavioral syndromes by administering to a subject in need thereof an effective amount of pipradrol or a pharmaceutically acceptable salt, derivative or analogue, or combination thereof, are provided. An effective amount or therapeutically effective amount can be a dosage sufficient to treat, inhibit, or alleviate one or more symptoms of a behavioral syndrome.

The precise dosage will vary according to a variety of factors such as subject-dependent variables (e.g., age, immune system health, clinical symptoms etc.). For example, the effect of a composition including pipradrol or a pharmaceutically acceptable salt, derivative or analogue thereof on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

Pipradrol or a pharmaceutically acceptable salt, derivative or analogue thereof as described herein may be considered stimulants because they "stimulate" motor behavior. These effects may come at a cost, since, in certain instances, stimulants can increase agitation and anxiety, reduce sleep, and inhibit appetite. Moreover, many can be addictive and have abuse potential. At higher doses stimulants may induce convulsions. On the simplest level, a stimulant may be considered to be the opposite of a depressant, and depressants, such as barbiturates and benzodiazepines may have robust anti-epileptic activity. Therefore, it is commonly believed that certain stimulants can be pro-convulsant and may typically be considered as contraindicated in the treatment of some disorders. Indeed, there is some clinical evidence that certain stimulants may lower the convulsive threshold in patients with prior history of seizures, in patients with prior electroencephalogram (EEG) abnormalities in the absence of seizures, and, rarely, in patients without a history of seizures and no prior EEG evidence of seizures.

In embodiments, compositions and methods of treatment are provided with low dosages of pipradrol such that the patient is provided one or more beneficial effects related to a behavioral syndrome, such as, reduced seizure activity, reduced fatigue, increased mood, increased concentration, increased behavioral control and/or increased cognitive ability. Pipradrol is known to have a relatively long half-life that may lead to prolonged effects and drug accumulation in a patient. Provided herein are dosing regimens that allow effective treatment of a behavioral syndrome with potentially limited or substantially few negative side effects, e.g., convulsions and/or sleep disruption. Accordingly, the methods described herein may provide treatment of a behavioral syndrome that may be considered surprising and unexpected. For example, methods are provided herein of treating behavioral syndromes in a patient in need thereof that may not cause sleep disruption. In embodiments, methods described herein may provide effective treatment of a behavioral syndrome without interrupting Slow Wave Sleep. In embodiments methods of treating a behavioral syndrome without causing insomnia or trouble falling asleep are provided. In some embodiments, methods are provided for treatment of sleep disorders, such as narcolepsy.

It is believed that the disclosed compounds, such as pipradrol, pharmaceutically acceptable salts, derivatives and/or analogues thereof, can be used as a monotherapy with pipradrol or a pharmaceutically acceptable salt thereof as the only active agent. For example, methods are provided of treating behavioral syndrome using pipradrol or a pharmaceutically acceptable salt thereof as the only active agent and a pharmaceutically acceptable carrier. In embodiments, methods of treating behavioral syndromes include administration of pipradrol, pharmaceutically acceptable salts, derivatives and/or analogues thereof in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of a behavioral syndrome with a combination of agents that combined, may provide a synergistic effect that enhances efficacy.

In embodiments, the disclosed methods include administering to a subject pipradrol in combination with gaboxadol. Gaboxadol, derivatives, analogues and structurally related compounds thereof useful in the disclosed methods includes any form of the compounds, such as the base (zwitterion), pharmaceutically acceptable salts, e.g., pharmaceutically acceptable acid addition salts, hydrates or solvates of the base or salt, as well as anhydrates, and also amorphous, or crystalline forms. In embodiments, a co-therapy of pipradrol or a derivative thereof and gaboxadol or a derivative thereof is effective to reduce seizure frequency or severity in the subject greater than either compound administered alone. In embodiments, the co-therapy produces a more than additive result compared to compounds administered individually.

In general, by way of example, dosage forms useful in the disclosed methods can include doses of gaboxadol, derivatives, analogues and structurally related compounds thereof in the range of 0.1 to 20 mg, 1 to 15 mg, 5 to 20 mg, 7.5 to 25 mg, or 10 to 30 mg, or 12.5 to 20 mg, or 15 to 25 mg, or 10 to 40 mg, or 5 to 50 mg, or 22.5 to 60 mg, or 25 to 50 mg, with doses of 1 mg, 5 mg, 10 mg, 15 mg, 20 mg, 25 mg, 30 mg, 35 mg, 40 mg, 45 mg, 50 mg, 55 mg, 60 mg, 75 mg, and 100 mg. Typically, such dosages are administered once, twice, or three times daily, or every other day to, e.g., a patient diagnosed with a behavioral syndrome.

An exemplary oral dose form may include from about 2.5 mg to about 30 mg gaboxadol. In embodiments, gaboxadol is in a crystalline form. In embodiments, the dosage form may include an effective amount of gaboxadol from 2.5 mg to 20 mg, such as 2.5 mg to 4 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg, e.g. 2.5 mg, 5 mg, 7.5 mg, 10 mg, 12.5 mg, 15 mg, 17.5 mg, or 20 mg. For example, a dosage form may include about 5 mg to about 20 mg of crystalline gaboxadol, such as the hydrochloride salt of gaboxadol. In embodiments, the total amount administered to a subject in 24-hour period is 1 mg to 50 mg. In embodiments, the subject may be started at a low dose and the dosage is escalated. In this manner, it can be determined if the drug is well tolerated in the subject. Dosages can be lower for children than for adults.

In embodiments, such as combination therapies, a dose of gaboxadol for children can be 0.1 mg/kg to 1 mg/kg, and the dose for pipradrol can be 0.01 mg/kg to 0.1 mg/kg. In embodiments, the weight/weight ratio of gaboxadol and pipradrol can be 10-to-1. However, the dosing ratio based on milligrams of active pharmaceutical ingredient (API) can range from 0.1-to-1 to 100-to-1 of gaboxadol-to-pipradrol respectively.

In embodiments, the disclosed methods include administering to a subject pipradrol in combination with acetazolamide, carbamazepine, clobazam, clonazepam, eslicarbazepine acetate, ethosuximide, gabapentin, lacosamide, lamotrigine, leviteracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Effective treatment of a behavioral syndrome (e.g., ADD or ADHD) herein may be established by showing reduction in the frequency or severity of one or more symptoms after a period of time compared with baseline. For example, after a baseline period of 1 month, the patients, after DSM-IV diagnoses of Attention Deficit Hyperactivity Disorder (ADHD) may be randomly allocated pipradrol or placebo. The patient's schoolteacher may complete the Conners ADHD/DSM-IV Scale for Teachers (CADS-T) at baseline and the end of each week. The CADS-T assesses symptoms of hyperactivity and inattention. The change from baseline of the (CADS-T) scores during the last week of treatment may be analyzed as the primary efficacy parameter. Symptoms of ADHD may also be evaluated by community schoolteachers using the Inattention/Overactivity with Aggression (IOWA) Conners scale or using the SKAMP laboratory school rating scale, which specifically measures the classroom manifestation of ADHD. Patients treated with pipradrol may show a statistically significant improvement in symptom scores from baseline over patients who received placebo.

The effectiveness of pipradrol for the treatment of a disclosed behavioral syndrome, e.g., ADHD, may be established in other controlled studies. A diagnosis of Attention Deficit Hyperactivity Disorder (ADHD; DSM-IV) implies the presence of hyperactive-impulsive or inattentive symptoms that caused impairment and were present before age 7 years. The symptoms must cause clinically significant impairment, e.g., in social, academic, or occupational functioning, and be present in 2 or more settings, e.g., school (or work) and at home. The symptoms must not be better accounted for by another mental disorder. For the Inattentive Type, at least 6 of the following symptoms must have persisted for at least 6 months: lack of attention to details/careless mistakes; lack of sustained attention; poor listener; failure to follow through on tasks; poor organization; avoids tasks requiring sustained mental effort; loses things; easily distracted; forgetful. For the Hyperactive-Impulsive Type, at least 6 of the following symptoms must have persisted for at least 6 months: fidgeting/squirming; leaving seat; inappropriate running/climbing; difficulty with quiet activities; "on the go;" excessive talking; blurting answers; can't wait turn; intrusive. The Combined Types requires both inattentive and hyperactive-impulsive criteria to be met.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s)

and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" are used herein interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods.

Those skilled in the art will recognize, or be able to ascertain using no more than routine experimentation, many equivalents to the embodiments described herein. Such equivalents are intended to be encompassed by the following claims.

The invention claimed is:

1. A method of treating Attention-Deficit Disorder including administering to a patient in need thereof a pharmaceutical composition consisting essentially of pipradrol or a pharmaceutically acceptable salt thereof.

2. The method of treating Attention-Deficit Disorder according to claim 1, wherein the patient is administered between about 1 mg and about 20 mg of the pipradrol or a pharmaceutically acceptable salt thereof.

3. The method of treating Attention-Deficit Disorder according to claim 2, wherein the patient is administered between about 1 mg and about 20 mg of the pipradrol or a pharmaceutically acceptable salt thereof once or twice daily.

4. The method of treating Attention-Deficit Disorder according to claim 1, wherein the patient is administered between about 0.1 mg and about 15 mg of the pipradrol or a pharmaceutically acceptable salt thereof.

5. The method of treating Attention-Deficit Disorder according to claim 4, wherein the patient is administered between about 0.1 mg and about 15 mg of the pipradrol or a pharmaceutically acceptable salt thereof once or twice daily.

6. The method of treating Attention-Deficit Disorder according to claim 1, wherein the patient is administered the pipradrol or a pharmaceutically acceptable salt thereof in an amount of 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, or 10 mg.

7. The method of treating Attention-Deficit Disorder according to claim 1, wherein the composition provides a prolonged effect.

8. The method of treating Attention-Deficit Disorder according to claim 1, wherein the composition provides reduction in hyperactivity, impulsiveness, inattentiveness, or a combination of symptoms in the patient.

9. A method of treating Attention-Deficit Hyperactivity Disorder including administering to a patient in need thereof a pharmaceutical composition consisting essentially of pipradrol or a pharmaceutically acceptable salt thereof.

10. The method of treating Attention-Deficit Hyperactivity Disorder according to claim 9, wherein the patient is administered between about 1 mg and about 20 mg of the pipradrol or a pharmaceutically acceptable salt thereof.

11. The method of treating Attention-Deficit Hyperactivity Disorder according to claim 10, wherein the patient is administered between about 1 mg and about 20 mg of the pipradrol or a pharmaceutically acceptable salt thereof once or twice daily.

12. The method of treating Attention-Deficit Hyperactivity Disorder according to claim 9, wherein the patient is administered between about 0.1 mg and about 15 mg of the pipradrol or a pharmaceutically acceptable salt thereof.

13. The method of treating Attention-Deficit Hyperactivity Disorder according to claim 12, wherein the patient is administered between about 0.1 mg and about 15 mg of the pipradrol or a pharmaceutically acceptable salt thereof once or twice daily.

14. The method of treating Attention-Deficit Hyperactivity Disorder according to claim 9, wherein the patient is administered the pipradrol or a pharmaceutically acceptable salt thereof in an amount of 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, or 10 mg.

15. The method of treating Attention-Deficit Hyperactivity Disorder according to claim 9, wherein the composition provides a prolonged effect.

16. The method of treating Attention-Deficit Hyperactivity Disorder according to claim 9, wherein the composition provides reduction in hyperactivity, impulsiveness, inattentiveness, or a combination of symptoms in the patient.

* * * * *